US011197766B1

(12) United States Patent
Suddaby

(10) Patent No.: US 11,197,766 B1
(45) Date of Patent: Dec. 14, 2021

(54) INTERVERTEBRAL DISC REPLACEMENT FUSION PROSTHESIS

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 0 days.

(21) Appl. No.: 17/179,878

(22) Filed: Feb. 19, 2021

(51) Int. Cl.
*A61F 2/44* (2006.01)
*A61F 2/30* (2006.01)

(52) U.S. Cl.
CPC ............ *A61F 2/4455* (2013.01); *A61F 2/441* (2013.01); *A61F 2/4425* (2013.01); *A61F 2002/30062* (2013.01); *A61F 2002/443* (2013.01)

(58) Field of Classification Search
CPC .......... A61F 2/44; A61F 2/442; A61F 2/4425; A61F 2002/443; A61F 2002/4445; A61F 2002/445; A61F 2002/4435; A61F 2/4455; A61F 2/441
USPC .......................................... 623/17.11–17.16
See application file for complete search history.

(56) References Cited

U.S. PATENT DOCUMENTS

| | | | |
|---|---|---|---|
| 6,969,405 B2 | 11/2005 | Suddaby | |
| 7,338,526 B2 | 3/2008 | Steinberg | |
| 8,062,368 B2 | 11/2011 | Heinz et al. | |
| 8,083,800 B2 | 12/2011 | Edie | |
| 8,147,555 B2 | 4/2012 | Kamran | |
| 8,632,592 B2 | 1/2014 | Barrall | |
| 8,915,963 B2 | 12/2014 | Aflatoon | |
| 8,940,052 B2 | 1/2015 | Lechmann et al. | |
| 8,974,528 B2 | 3/2015 | Cheng | |
| 9,561,117 B2 | 2/2017 | Lechmann et al. | |
| 9,827,109 B2 | 11/2017 | Steinberg | |
| 10,058,433 B2 | 8/2018 | Lechmann et al. | |
| 2008/0058931 A1 | 3/2008 | White et al. | |
| 2009/0248159 A1* | 10/2009 | Aflatoon | A61F 2/442 623/17.12 |
| 2012/0191189 A1* | 7/2012 | Huang | A61F 2/4425 623/17.11 |

FOREIGN PATENT DOCUMENTS

| | | |
|---|---|---|
| CN | 107049565 | 8/2017 |
| WO | WO2007/076374 | 7/2007 |

* cited by examiner

*Primary Examiner* — Eduardo C Robert
*Assistant Examiner* — Christina Negrellirodriguez
(74) *Attorney, Agent, or Firm* — Simpson & Simpson, PLLC; Michael Nicholas Vranjes

(57) ABSTRACT

An motion preserving intervertebral disc replacement/fusion prosthesis, including an inferior component, including a first top surface, a first bottom surface, a chamber arranged between the first top surface and the first bottom surface, and a plurality of apertures extending from the first bottom surface to the chamber, a superior component, including a second top surface, and a second bottom surface, and a spacing element arranged between the first top surface and the second bottom surface. The prosthesis is arranged to allow a fusion or similar stable union between the prosthetic surfaces and adjacent vertebra elements, while allowing for normal motion between adjacent vertebrae once stable union between the prosthesis and the juxtaposed vertebral endplate and the prosthesis occurs, such union being facilitated by bio absorbable struts that prevent motion until device/endplate union is solid, but permitting fully normal range of motion of the device once strut dissolution has occurred.

18 Claims, 9 Drawing Sheets

INTERVERTEBRAL DISC REPLACEMENT FUSION PROSTHESIS

FIELD

The present disclosure relates to orthopedic surgery, and more particularly to a prosthetic intervertebral disc replacement system which can be implanted into a suitably prepared intervertebral disc space via minimally invasive surgical techniques to provide for and restore substantial functional normalcy, with all the stability afforded by a spinal fusion and all the benefits of normal motion.

BACKGROUND

The spinal column, or backbone, is one of the most important parts of the body. It provides the main support, allowing us to stand upright, bend, and twist. As shown in FIG. 1, thirty-three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

The normal intervertebral disc is in essence a complex joint which allows for various articular motions between adjacent vertebral segments. These articular motions, in turn, account for the flexibility and functional mobility of the normal human spine. In the course of a day, the normal intervertebral disc encounters a variety of compressional, rotational, and associated flexion or extension movements. In these day-to-day activities, movements in varying and repetitive combinations accumulate and contribute to the deterioration of natural discs that occurs over time. As with other joints in the human body that deteriorate over time, it would be desirable to have disc replacement prostheses that could be inserted in place of a failed or worn normal disc when it is determined the disc is irreparably damaged and that preservation of functional mobility is required.

The time-honored method of addressing debilitating symptoms and signs of a degenerative disc is to remove the disc and fuse the two adjacent vertebral bodies together. Fusion eliminates motion at the abnormal segment, and while useful at improving debilitating symptoms of back pain, the consequence of eliminating natural motions at a single segment is that greater degrees of stress occur above and below that segment. This in turn accelerates degeneration of neighboring intervertebral discs, often necessitating additional fusion surgeries.

It would be desirable, therefore, to preserve motion at every disc space and thus retain natural motion, while eliminating the adjacent level degeneration that discectomy and fusion seems to produce. Toward this end, an intervertebral disc replacement prosthesis ought ideally to restore and preserve normal disc space height while permitting sufficient natural motion (flexion, extension, rotation, and lateral bending) to prevent excessive stresses on spinal segments above and below the prosthesis.

Several intervertebral disc replacement prostheses are now being marketed, but none have achieved the predictable efficacy and reliability of interbody fusion. The reasons for this, and the reluctance of surgeons to adopt total mobile disc replacements are that most if not all of these replacements fail to provide lasting functional alignment or long-term relief of axial back pain, similar to that afforded by a successful spinal fusion.

Part of the failure stems from the misconception that the intervertebral disc is the sole dictator of movement that occurs at the intervertebral level, when, in reality, it is the ligaments surrounding the disc that are the arbiters of normal spinal movement. That is to say, the soft gelatinous nucleus of a disc provides little if any orchestration of movement, but rather serves as a flexible spacer to maintain a normal set distance between vertebral segments such that the ligaments, which function best in tension, can suitably restrict relative motion in a manner that allows normal movement, maintains facet joint alignment, and restricts spatial relations to degrees which prevent neural injury. Ligaments define motion, and nuclear material permits motion by keeping the ligaments suitably taut and providing a flexible and forgiving center of rotation, around which, flexion, extension, rotation, lateral bending, and translation occur.

The second misconception is that discs function as important shock absorbers to presumably protect the brain or perhaps adjacent structures from trauma. While this may be partially true in human spines insofar as they have larger amounts of gelatinous nuclear material contained within a disc, it is also clear that substantial amounts of soft nuclear material exists in vertebrates, which have no or little axial loading of their spines and are largely held in a horizontal attitude life-long. Since discs are arranged in series, the absence of one or two cushions in what amounts to a stack of two dozen, results in little in the way of inhibiting meaningful shock absorption.

It is apparent, therefore that the spongiform nucleus plays a decidedly different role than simple shock mitigation. Indeed, looking at the largely avascular structure of the intervertebral disc and its reliance on diffusion from endplates for nourishment of the sparse cells contained therein, the compression and relaxation cycles afforded by motion, whether in a vertical or horizontal position, act as a type of bellows, the purpose of which is to draw in or expel nutrients into or out of what is essentially a large hypoxic and avascular organ structure. Cushioning, as evidenced from comparative vertebrate anatomy, would hence be a recent and relatively less important evolutionary accoutrement. Indeed, the intervertebral disc is the largest avascular structure in the human body, next to the lens of the eye.

Furthermore, in direct contradiction to the edict that ligaments define motion, most total mobile disc replacements are inserted anteriorly, necessitating the transection of the anterior longitudinal ligament which is perhaps the strongest of the stabilizing and interconnecting spinal ligaments. Once this is done to insert the device, anterior spinal stability is irretrievably lost, and this is particularly notable when the spine is extended, rather than flexed.

Consequentially, current total disc replacement surgeries done to address the micro instability of a degenerative spine may actually make symptoms worse through direct violation of this most critical stabilizing ligament (i.e., replacing micro instability with macro instability). In addition, since repetitive motion at the surgical level continuously impacts hard metal artificial endplates against softer bone, subsidence and shifting of the device within the interspace frequently occurs. Any metal construct inserted into or apposed to the bone will loosen unless a stable bone to implant (fusion) integration occurs. An artificial disc bone interface is subjected almost immediately to moment forces secondary to the movement of the device, subjecting the device/endplate union to repetitive movement. This continuous movement works contrary to restricted motion seen at fusion device/endplate interfaces and encourages device loosening.

Clearly, there is a need within the art and science of surgery to replace a damaged intervertebral disc without violating critical movement determining structures (e.g., ligaments), without the need for the perilous displacement of organs (e.g., arteries, veins, intestines), and without subjecting delicate endplates to repetitive mechanical trauma from the shifting vector forces of rigid unforgiving metal endplates. Thus, there is a long-felt need for an intervertebral disc replacement prosthesis that does not restrict normal disc and vertebral movement and utilizes fusion to prevent such mechanical trauma.

SUMMARY

According to aspects illustrated herein, there is provided an intervertebral disc replacement fusion prosthesis, comprising an inferior component, including a first top surface, a first bottom surface, a chamber arranged between the first top surface and the first bottom surface, and a plurality of apertures extending from the first bottom surface to the chamber, a superior component, including a second top surface, and a second bottom surface, and a spacing element arranged between the first top surface and the second bottom surface.

In some embodiments, the spacing element comprises an inflatable sac. In some embodiments, the prosthesis further comprises at least one first groove arranged in the first top surface, at least one second groove arranged in the second bottom surface, and a strut operatively arranged to engage the at least one first groove and the at least one second groove. In some embodiments, the strut prevents the superior component from displacing toward and circumferentially with respect to the inferior component. In some embodiments, the strut is absorbable or dissolvable. In some embodiments, the prosthesis further comprises at least one flange extending from at least one of the inferior component and the superior component. In some embodiments, the at least one flange extends from the inferior component and comprises an aperture fluidly connected to the chamber. In some embodiments, the prosthesis further comprises a first insert slidingly engaged with the first top surface, the first insert including a first inner surface engaged with the spacing element, and a second insert slidingly engaged with the second bottom surface, the second insert including a second inner surface engaged with the spacing element. In some embodiments, the first inner surface and the second inner surface are concave. In some embodiments, the spacing element is convex in shape at its engagement with the first inner surface and the second inner surface. In some embodiments, the first inner surface and the second inner surface are slidingly engaged with the spacing element.

According to aspects illustrated herein, there is provided an intervertebral disc replacement fusion prosthesis, comprising an inferior component, including a first top surface, a first bottom surface, a first chamber arranged between the first top surface and the first bottom surface, and a first plurality of apertures extending from the first bottom surface to the first chamber, a superior component, including a second top surface, a second bottom surface, a second chamber arranged between the second top surface and the second bottom surface, and a second plurality of apertures extending from the second bottom surface to the second chamber, and a spacing element arranged between the first top surface and the second bottom surface, wherein the superior component is translationally and circumferentially displaceable relative to the inferior component.

In some embodiments, the spacing element comprises an inflatable sac. In some embodiments, the prosthesis further comprises at least one first groove arranged in the first top surface, at least one second groove arranged in the second bottom surface, and a strut operatively arranged to engage the at least one first groove and the at least one second groove. In some embodiments, the strut prevents the superior component from displacing toward and circumferentially with respect to the inferior component. In some embodiments, the strut is totally absorbable or dissolvable. In some embodiments, the prosthesis further comprises at least one flange extending from the inferior component, the at least one flange comprising an aperture fluidly connected to the first chamber. In some embodiments, the prosthesis further comprises a first insert slidingly engaged with the first top surface, the first insert including a first concave inner surface engaged with the spacing element, and a second insert slidingly engaged with the second bottom surface, the second insert including a second concave inner surface engaged with the spacing element. In some embodiments, the spacing element is convex in shape at its engagement with the first inner surface and the second inner surface, and the first inner surface and the second inner surface are slidingly engaged with the spacing element.

According to aspects illustrated herein, there is provided an intervertebral disc replacement fusion prosthesis, comprising an inferior component, including a first top surface, a first bottom surface, a first chamber arranged between the first top surface and the first bottom surface, and a first plurality of apertures extending from the first bottom surface to the first chamber, a superior component, including a second top surface, a second bottom surface, a second chamber arranged between the second top surface and the second bottom surface, and a second plurality of apertures extending from the second bottom surface to the second chamber, a first insert slidingly engaged with the first top surface, a second insert slidingly engaged with the second bottom surface, and an inflatable sac arranged between the first insert and the second insert, wherein in an unlocked state, the superior component is translationally and circumferentially displaceable relative to the inferior component, and in a locked state, at least one strut is engaged with the first top surface and the second bottom surface to prevent the superior component from displacing toward and circumferentially with respect to the inferior component.

According to aspects illustrated herein, there is provided an intervertebral disc replacement prosthesis which combines elements of vertebral interbody fusion along with all of the cardinal movements afforded by normal intervertebral discs such that a stable disc replacement construct can be obtained that provides all of the benefits of interbody fusion with all the advantages of motion preservation through the principles of stable bone/prosthesis interfaces with controlled adjustable ligamentous tensioning such that disc height can be restored, facet joints returned to functional alignment and secondary degenerative changes mitigated by restoration of normal anatomic relationships, customizable to the specific disc height of an individual patient.

It is the object of the present disclosure to provide for a complete and functional disc replacement that adheres to the tenet that it is the ligament(s) that determines the normal functional relationship between mobile vertebrae segments and that preservation of these ligaments is critical to the success of effective and reproducible clinical disc replacement surgery.

It is also an object of the present disclosure that the prosthesis restore proper tautness to intervertebral ligaments such that they can be restored to functional normalcy. It is a further objective that the insertion of the total disc replacement prosthesis be accomplished via an approach that avoids critical internal structures and preserves the anterior and posterior ligaments of the spine, as well as the posterior elements (e.g., facet joints and spinous processes) which are most crucial to spinal movement and stability.

To achieve these objectives, the present disclosure includes an intervertebral prosthetic device comprising two fixed endplate components that can be bonded to the adjacent vertebrae through the process of bony fusion. Between the endplate components is an expandable core infinitely adjustable through hydraulic or mechanical means to restore paraspinal support ligaments to their optimal tautness. The inflatable core has wear surfaces between the adjacent end plate components and itself permitting the cardinal dimensions of normal motion to occur. The core itself is composed of a pre-configured cranial and caudal wear surface which interfaces with the endplate component to permit pre-determined motions such as flexion, extension, rotation, and lateral bending within normal degrees. By allowing the core to translate in multiple directions, a changeable center of rotation mimicking the natural state can be achieved. While in some embodiments an expandable insertable wear surface is used, it is also recognized that such a variable fit can be achieved by static deployable wear-surfaced inserts, provided that multiple core sizes be available to achieve that purpose.

The portion of the core between the endplates, in some embodiments, is an inflatable sac which permits insufflation with a hardenable material that displaces adjacent wear surfaces from each other sufficient to restore normal disc height as determined by observation (radiographic) and ligamentous tautness, as determined by infusion pressure or volume. Once proper intervertebral distance (i.e., disc height) has been restored, the preserved ligaments can orchestrate normal motion as provided by the attached muscles of the spinal elements.

The endplate contacts of the device are also unique insofar as they contain cavities which can be prefilled with allograft bone to encourage ingrowth of bone into the prosthetic endplate to achieve long-term stability and thwart subsidence. Additionally, the surface of the device endplate will contain favorable macro and microscopic architecture to favor bone to implant apposition, and/or applies surface materials such as hydroxyapatite which favors bone to construct integration and stability. In this manner, the long-term stability of an interbody fusion device can be combined with the movement capability of a total disc replacement to achieve the positive results of both surgical solutions. Loosening and migration can be thwarted while motion is maintained.

To preserve the anterior and posterior ligaments of the spine, the device will be inserted in a manner such that major ligaments are preserved, for example, lateral, antero-lateral or postero-lateral.

To aid in endplate union and stability to bone prior to subjecting the region to repetitive motion, the device will contain absorbable implanted struts placed anteriorly and posteriorly to restrict motion for approximately three months, during which time bonding or fusion of the device endplate to the vertebral body endplate can occur. By doing this, subsidence, and device placement and aberrant device bone interface disruption can be mitigated. Such struts can be formed of resorbable polylactic acid and polyglycolic acid.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

Figure 1:
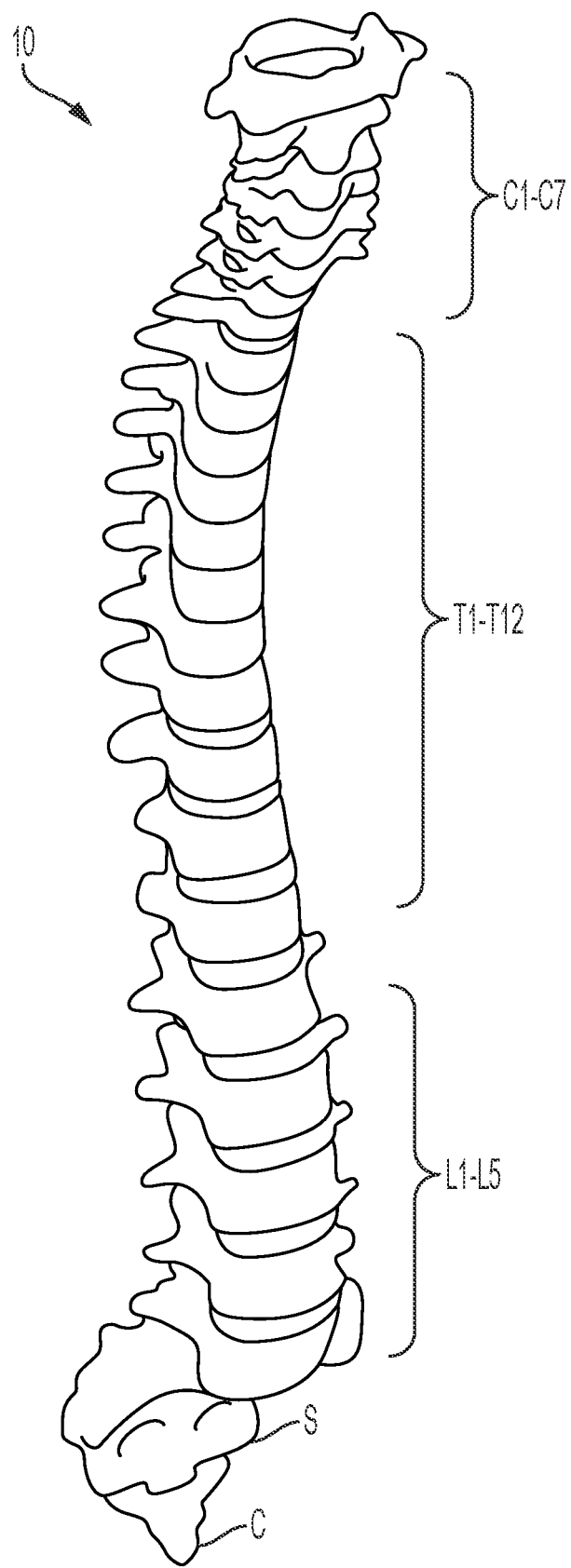
FIG. 1 is an anterior perspective view of a spinal column.
Figure 2:
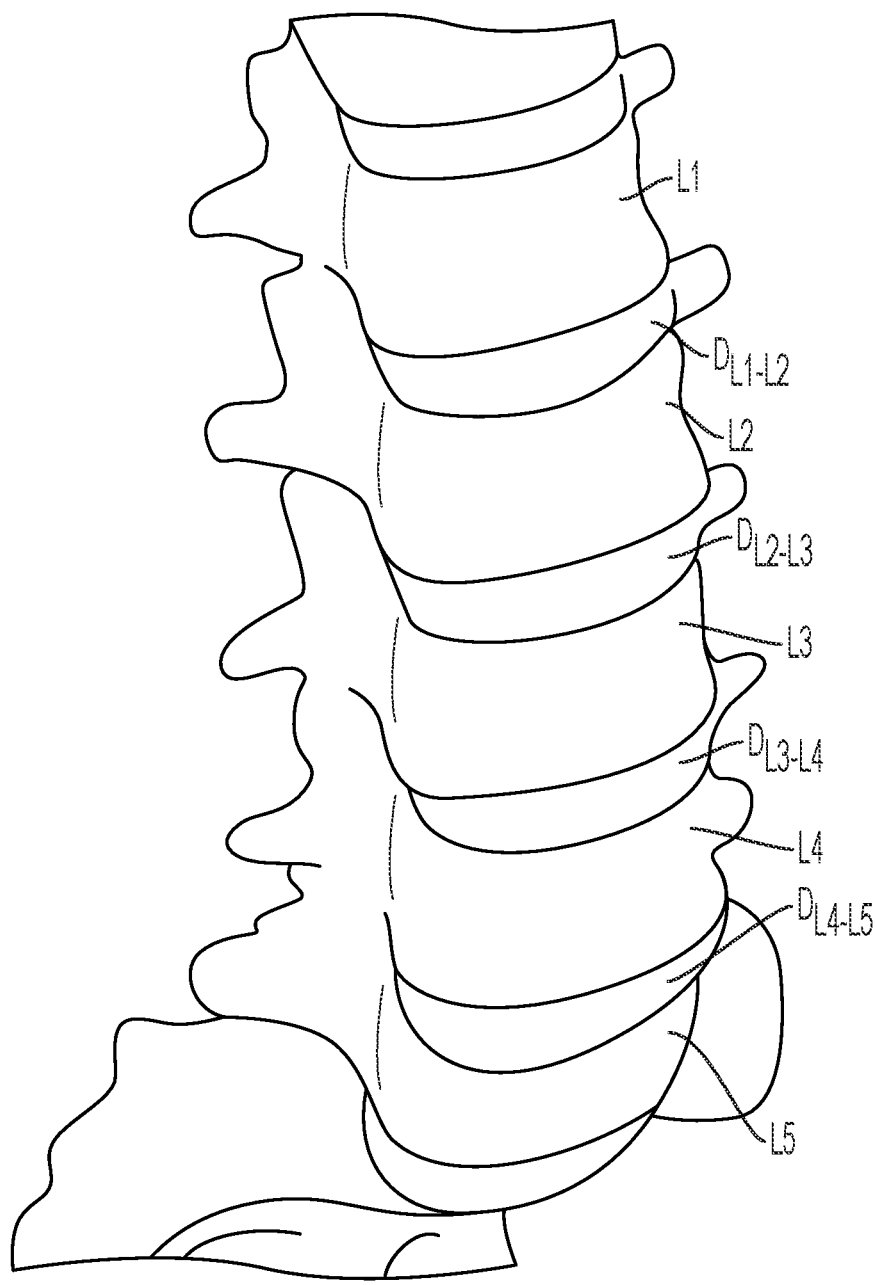
FIG. 2 is an anterior perspective view of the lumbar section of the spinal column shown in FIG. 1.
Figure 3:
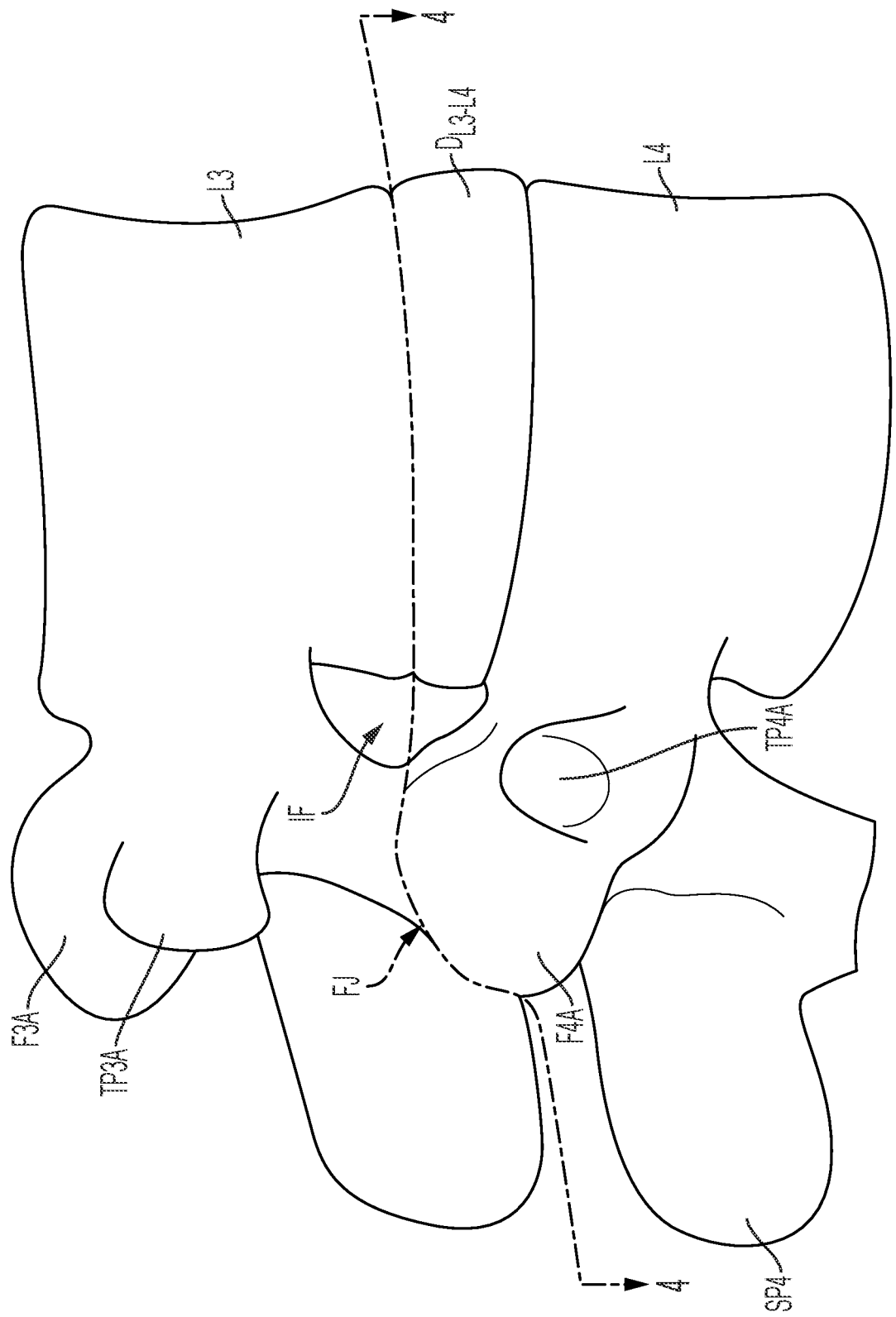
FIG. 3 is a lateral perspective view of two vertebrae, a disc, and related spinal anatomy.
Figure 4:
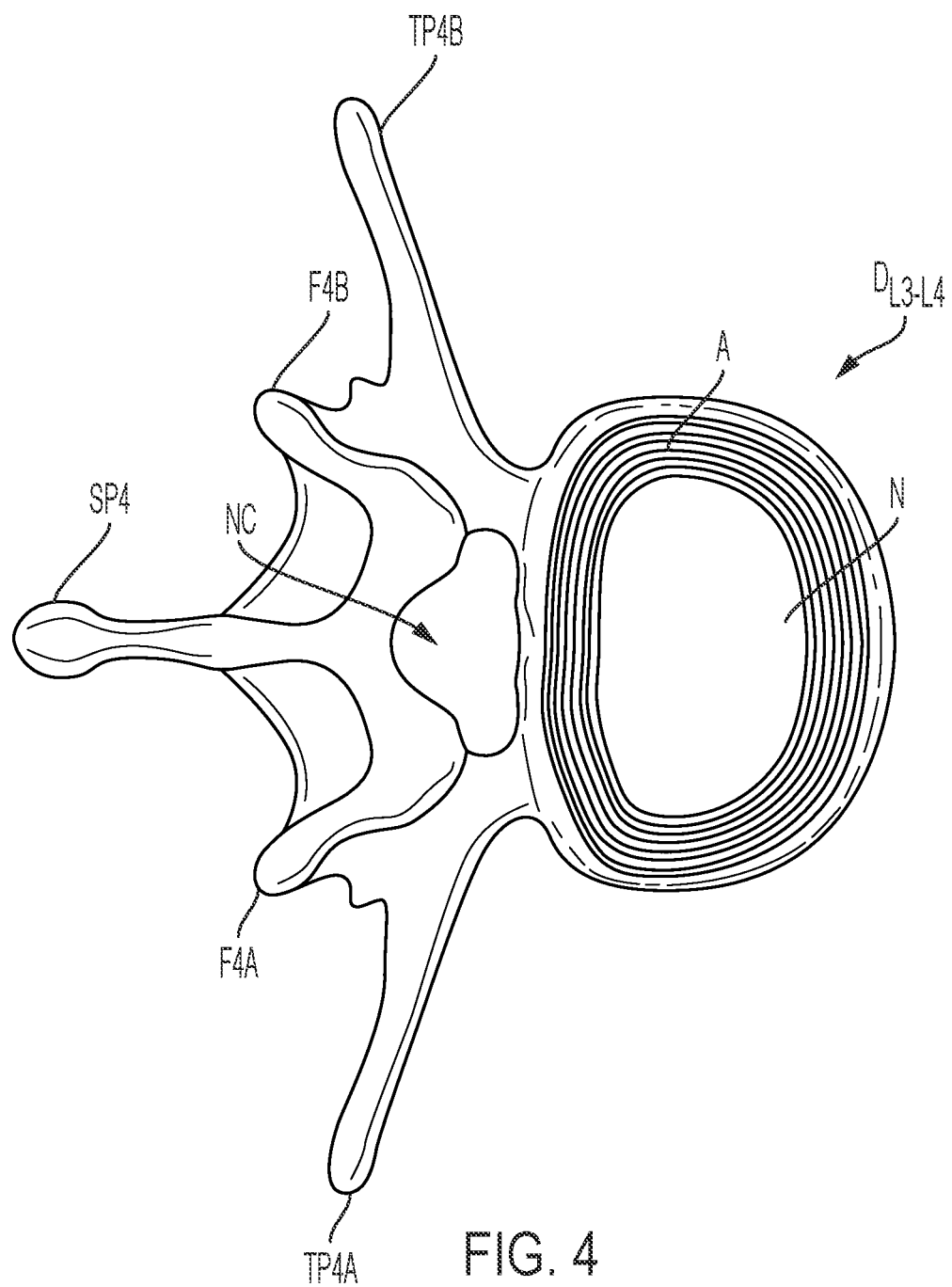
FIG. 4 is a top view of a section of the spinal column, taken generally along line 4-4 in FIG. 3.
Figure 5:
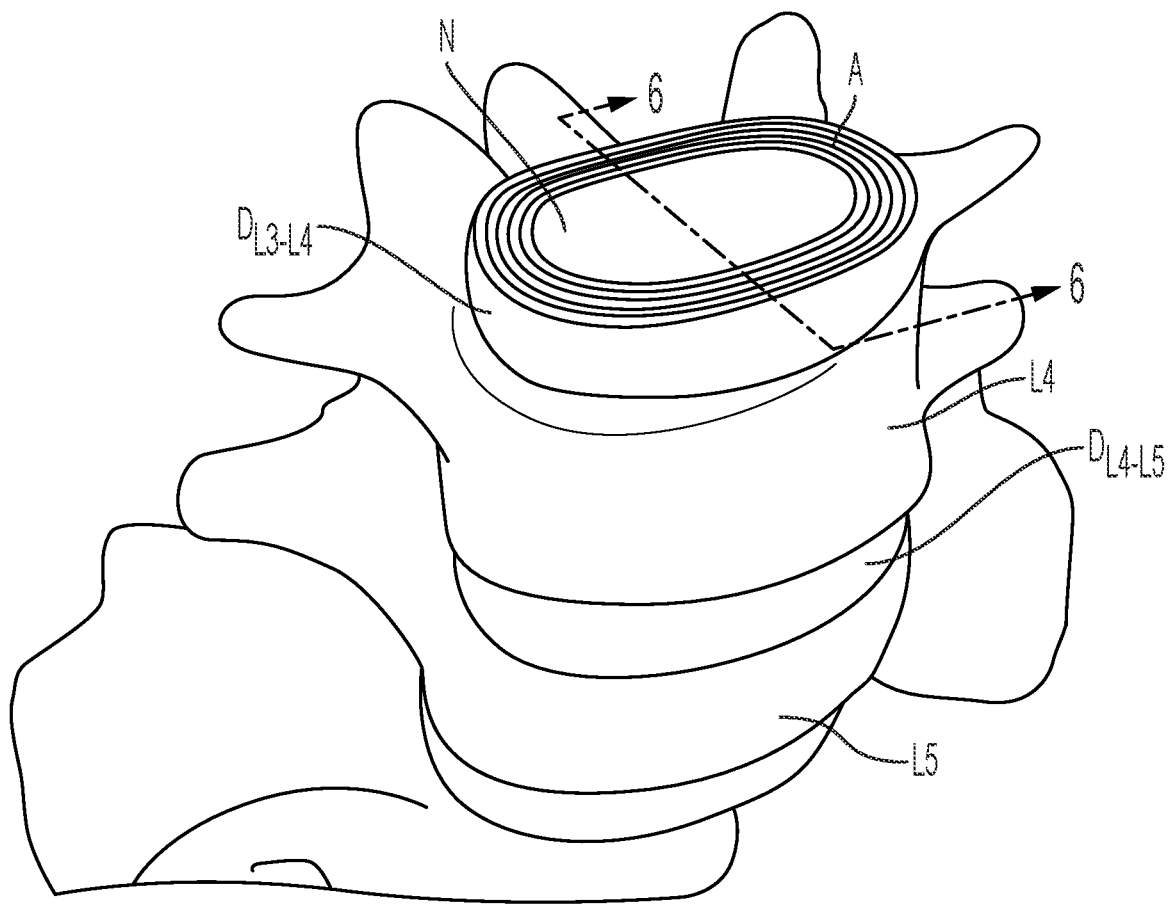
FIG. 5 is an enlarged anterior perspective view of the spinal column shown in FIG. 2, except with the top vertebra and all other structure above the top vertebra removed.
Figure 6:
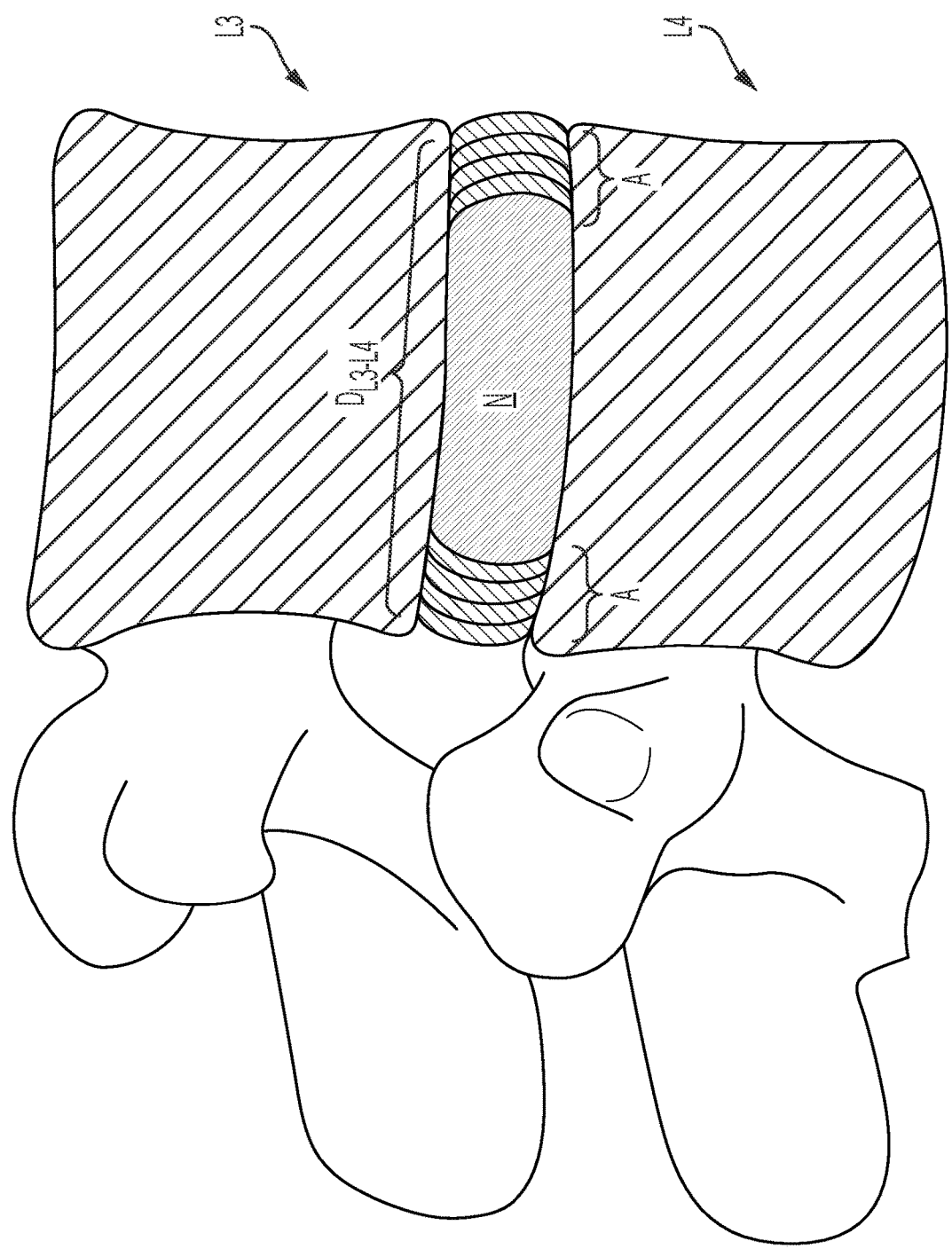
FIG. 6 is a partial cross-sectional view of the top and bottom vertebrae and disc, taken generally along line 6-6 in FIG. 5.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

By "non-rotatably connected" elements, we mean that: the elements are connected so that whenever one of the elements rotate, all the elements rotate; and, relative rotation between the elements is not possible. Radial and/or axial movement of non-rotatably connected elements with respect to each other is possible, but not required. By "rotatably connected" elements, we mean that: the elements are rotatable with respect to each other; and, whenever one element is displaced radially and/or axially, all the elements are displaced radially and/or axially.

Figure 7A:
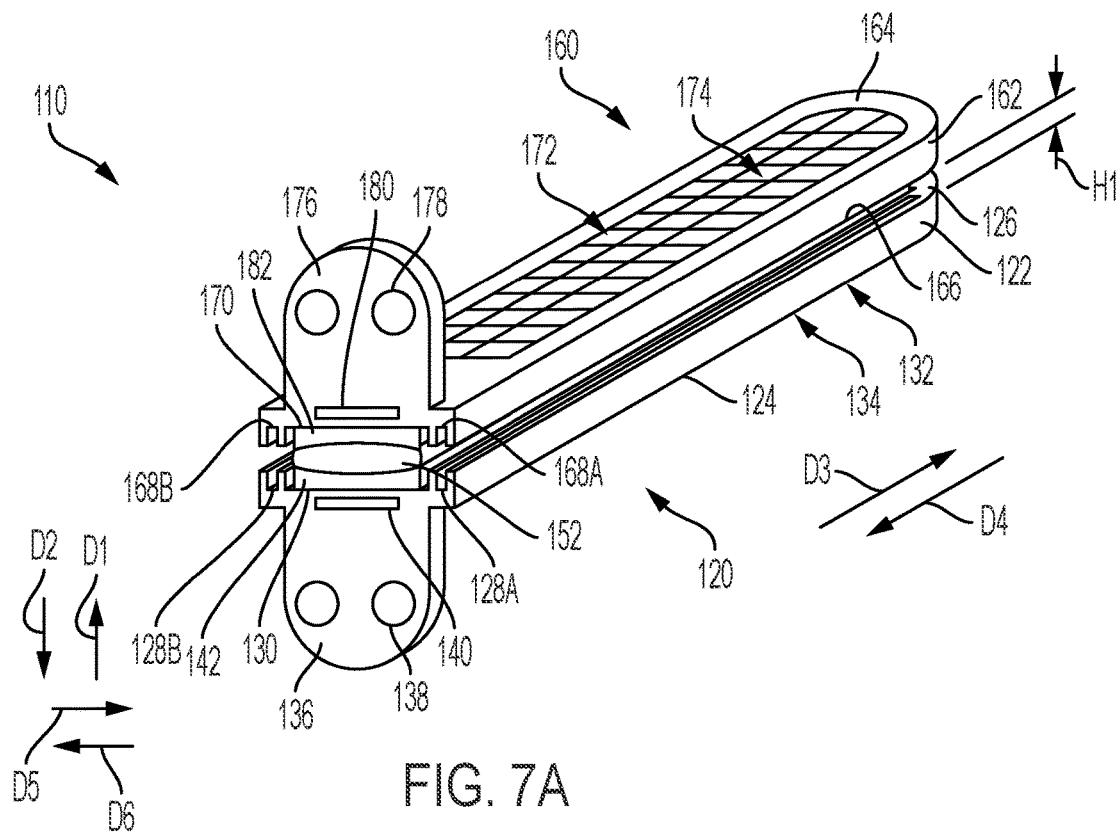
FIG. 7A is a perspective view of an intervertebral disc replacement fusion prosthesis, in a collapsed state.
Figure 7B:
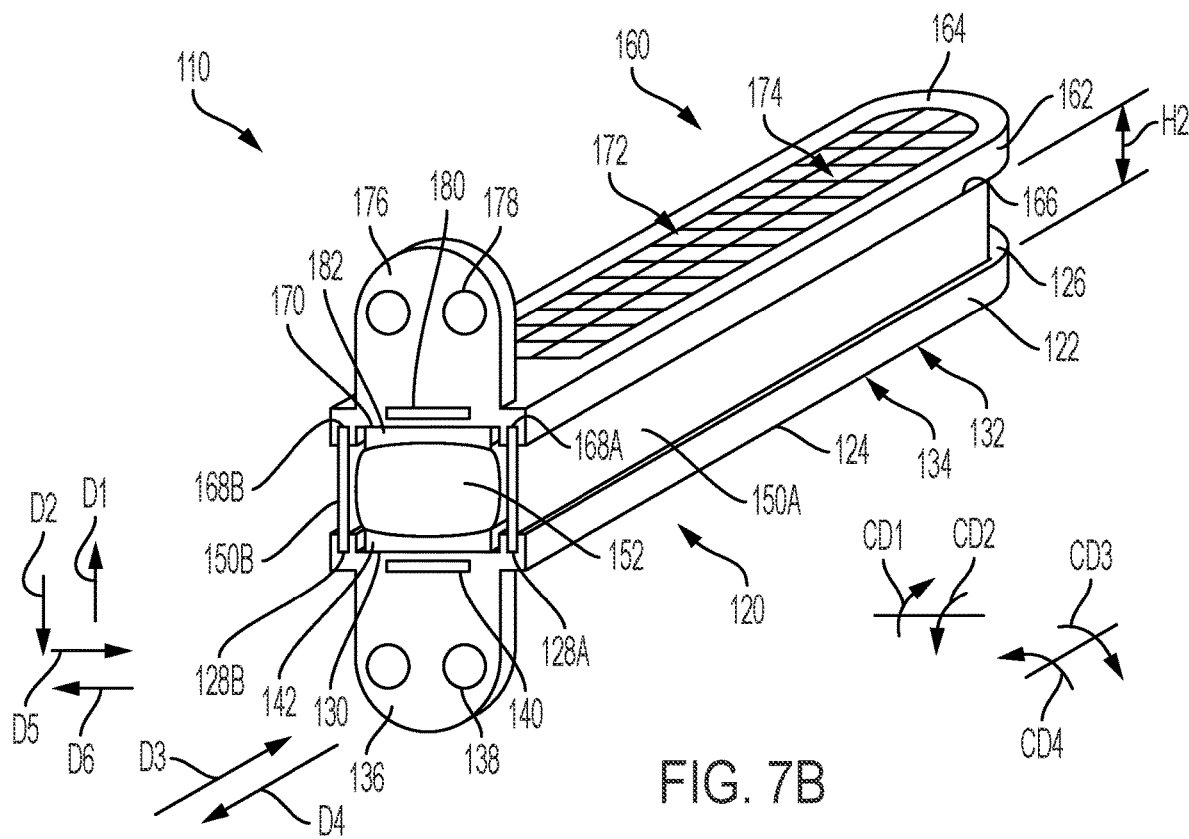
FIG. 7B is a perspective view of the intervertebral disc replacement fusion prosthesis shown in FIG. 7A, in an expanded state.
Figure 8:
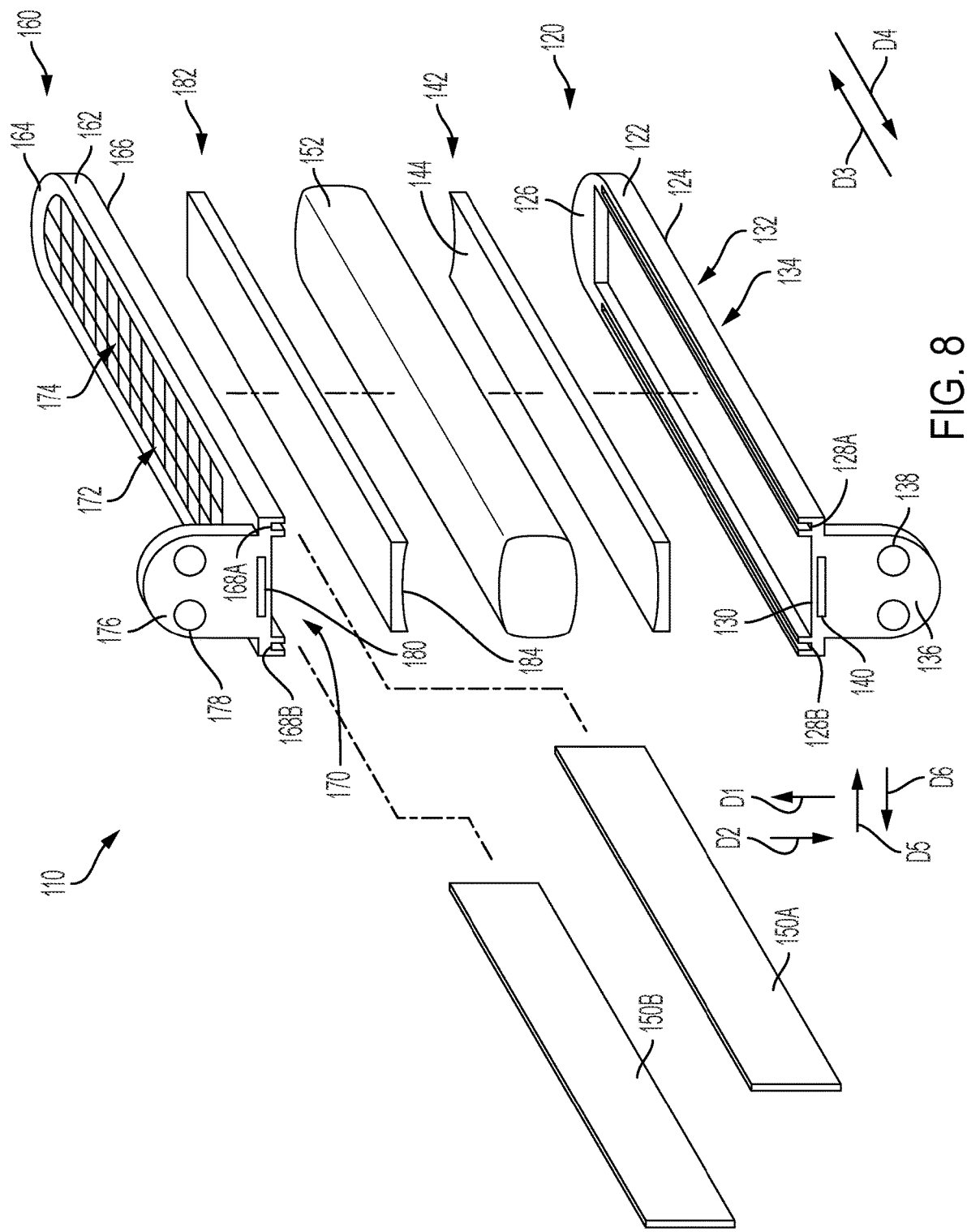
FIG. 8 is an exploded perspective view of the intervertebral disc replacement fusion prosthesis shown in FIGS. 7A-B.

Adverting now to the figures, and as described previously, FIGS. 1-6 depict various parts and sections of spinal anatomy. FIG. 7A is a perspective view of intervertebral disc replacement fusion prosthesis 100, in a collapsed state. FIG. 7B is a perspective view of intervertebral disc replacement fusion prosthesis 110, in an expanded state. FIG. 8 is an exploded perspective view of intervertebral disc replacement fusion prosthesis 110. Intervertebral disc replacement fusion prosthesis, or prosthesis 110, generally comprises inferior component 120, superior component 160, and a spacing element, for example, inflatable sac 152. In some embodiments, prosthesis 110 further comprises insert 142 and insert 182. The following description should be read in view of FIGS. 7A-8.

Inferior component 120 comprises body 122 and flange 136. Body 122 comprises surface 124 operatively arranged to engage an adjacent vertebra and surface 126 operatively arranged to engage inflatable sac 152. As such, surface 124 is said to be the outer surface of inferior component 120 and surface 126 is said to be the inner surface of inferior component 120. Surface 124 comprises chamber 132 which extends in direction D1 therefrom. Chamber 132 opens to surface 124 via a plurality of apertures 134. Chamber 132 and apertures 134 are substantially the same as chamber 172 and apertures 174, respectively, as shown in superior component 160. In some embodiments, apertures 134 may be arranged as mesh or a grate or a grill over chamber 132. For example, chamber 132 may be formed in surface 124, and mesh (or a screen, grate, grill, etc.) is then arranged over chamber 132 at surface 124. In some embodiments, chamber 132 is formed from flange 136. A chamber can be carved into body 122 from the proximal end of inferior component 120 in direction D3, after which a plurality of windows or apertures or holes 134 are created in surface 124 and extend to chamber 132. It should be appreciated that apertures 134 are operatively arranged to allow bone material, arranged in chamber 132, to fuse with a vertebra adjacent to surface 124 such that inferior component 120 fuses with the adjacent vertebra. In some embodiments, surface 124 is porous thereby allowing liquid or air to pass therethrough (i.e., porous bone windows). This facilitates bone ingrowth into prosthesis 110, specifically, inferior component 120.

Surface 126 comprises groove 128A proximate a first lateral edge of inferior component 120 and groove 128B proximate a second lateral edge of inferior component 120, opposite the first lateral edge. Grooves 128A-B extend from surface 126 in direction D2. Grooves 128A and 128B are operatively arranged to engage struts 150A and 150B, respectively, as will be described in greater detail below. Surface 126 further comprises groove 130 operatively arranged to engage inflatable sac 152.

In some embodiments, insert 142 is arranged in groove 130. Insert 142 comprises surface 144 operatively arranged to engage inflatable sac 152. Insert 182 provides a wear surface or layer between superior component 160 and inflatable sac 152. In some embodiments, surface 144 is curvilinear, for example concave. Surface 144 is operatively arranged to engage a generally convex sac 152 to provide normal disc movement of inferior component 120 relative to sac 152, and thus superior component 160. For example, the engagement of surface 144 and sac 152 allows for rotational displacement of inferior component 120 relative to sac 152 in all circumferential directions, for example, and inter alia, circumferential directions CD1-4. Additionally, the engagement of surface 144 and sac 152 allows for translational displacement of inferior component 120 relative to sac 152 in all linear directions, for example, and inter alia, directions D1-6. It should be appreciated that, in some embodiments, insert 142 comprises a material softer than body 122 and inflatable sac 152 (i.e., the hardenable material within sac 152), such that any wear that occurs is imparted upon insert 142 and not body 122 or inflatable sac 152. Since wear is the damaging, or gradual removal or deformation of material at solid surfaces caused by mechanical interaction between components, directing wear to occur at insert 142 maintains the structural integrity of body 122 and inflatable sac 152. In some embodiments, surface 126 is concave and directly engages inflatable sac 152 without the need for an insert.

It should also be appreciated that in some embodiments, insert 142 is slidably engaged with groove 130. In some embodiments, the width of insert 142 is less than the width of groove 130, creating translation space. Translation space refers to the space between the lateral sides of insert 142 and the edges of groove 130, in directions D5 and D6. The translation space or spaces allow for inferior component 120 to slide in directions D5 and D6 relative to insert 142 and inflatable sac 152. Such design allows for greater translational movement of inferior component 120 and its adjacent vertebra, relative to inflatable sac 152 and superior component 160.

Flange 136 is connected to a proximal end of inferior component 120 and extends therefrom generally in direction D2. Flange 136 comprises at least one hole, for example holes 138, operatively arranged to engage a fixation device to secure inferior component 120 to the adjacent vertebra. In some embodiments, flange 136 is arranged substantially perpendicular to body 122, specifically, surface 124. In some embodiments, flange 136 is arranged non-perpendicular to surface 124. Flange 136 further comprises aperture 140. Aperture 140 extends through flange 136 in direction D3 and is fluidly connected to chamber 132. As will be described in greater detail below, once prosthesis 110 properly arranged at the desired height between vertebrae, bone material (e.g., allograph bone) can be inserted into chamber 132 via aperture 140.

Superior component 160 comprises body 162 and flange 176. Body 162 comprises surface 164 operatively arranged to engage an adjacent vertebra and surface 166 operatively arranged to engage inflatable sac 152. As such, surface 164 is said to be the outer surface of superior component 160 and surface 166 is said to be the inner surface of superior component 160. Surfaces 164 and 124 face away from each other and surfaces 166 and 126 face toward each other. Surface 164 comprises chamber 172 which extends in direction D2 therefrom. Chamber 172 opens to surface 164 via a plurality of apertures 174. In some embodiments, apertures 174 may be arranged as mesh or a grate or a grill over chamber 172. For example, chamber 172 may be formed in surface 164, and mesh (or a screen, grate, grill, etc.) is then arranged over chamber 172 at surface 164. In some embodiments, chamber 172 is formed from flange 176. A chamber can be carved into body 162 from the proximal end of superior component 160 in direction D3, after which a plurality of windows or apertures or holes 174 are created in surface 164 and extend to chamber 172. It should be appreciated that apertures 174 are operatively arranged to allow bone material, arranged in chamber 172, to fuse with a vertebra adjacent to surface 164 such that superior component 160 fuses with the adjacent vertebra. In some embodiments, surface 164 is porous thereby allowing liquid or air to pass therethrough (i.e., porous bone windows). This facilitates bone ingrowth into prosthesis 110, specifically, superior component 160.

Surface 166 comprises groove 168A proximate a first lateral edge of superior component 160 and groove 168B proximate a second lateral edge of superior component 160, opposite the first lateral edge. Grooves 168A-B extend from surface 166 in direction D1. Grooves 168A and 168B are operatively arranged to engage struts 150A and 150B, respectively, and to align with grooves 128A and 128B, respectively, as will be described in greater detail below. Surface 166 further comprises groove 170 operatively arranged to engage inflatable sac 152.

In some embodiments, insert 182 is arranged in groove 170. Insert 182 comprises surface 184 operatively arranged to engage inflatable sac 152. Insert 182 provides a wear surface or layer between superior component 160 and inflatable sac 152. In some embodiments, surface 184 is curvilinear, for example concave. Surface 184 is operatively arranged to engage a generally convex sac 152 to provide normal disc movement of superior component 160 relative to sac 152, and thus inferior component 120. For example, the engagement of surface 184 and sac 152 allows for rotational displacement of superior component 160 relative to sac 152 in all circumferential directions, for example, and inter alia, circumferential directions CD1-4. Additionally, the engagement of surface 184 and sac 152 allows for translational displacement of superior component 160 relative to sac 152 in all linear directions, for example, and inter alia, directions D1-6. It should be appreciated that, in some embodiments, insert 182 comprises a material softer than body 162 and inflatable sac 152 (i.e., the hardenable material within sac 152), such that any wear that occurs is imparted upon insert 182 and not body 162 or inflatable sac 152. Since wear is the damaging, or gradual removal or deformation of material at solid surfaces caused by mechanical interaction between components, directing wear to occur at insert 182 maintains the structural integrity of body 162 and inflatable sac 152. In some embodiments, surface 166 is concave and directly engages inflatable sac 152 without the need for an insert.

It should also be appreciated that in some embodiments, insert 182 is slidably engaged with groove 170. In some embodiments, the width of insert 182 is less than the width of groove 170, creating translation space. Translation space refers to the space between the lateral sides of insert 182 and the edges of groove 170, in directions D5 and D6. The translation space or spaces allow for superior component 160 to slide in directions D5 and D6 relative to insert 182 and inflatable sac 152. Such design allows for greater translational movement of superior component 160 and its adjacent vertebra, relative to inflatable sac 152 and inferior component 120.

Flange 176 is connected to a proximal end of superior component 160 and extends therefrom generally in direction D1. Flange 176 comprises at least one hole, for example holes 178, operatively arranged to engage a fixation device to secure superior component 160 to the adjacent vertebra. In some embodiments, flange 176 is arranged substantially perpendicular to body 162, specifically, surface 164. In some embodiments, flange 176 is arranged non-perpendicular to surface 164. Flange 176 further comprises aperture 180. Aperture 180 extends through flange 176 in direction D3 and is fluidly connected to chamber 172. As will be described in greater detail below, once prosthesis 110 properly arranged at the desired height between vertebrae, bone material (e.g., allograph bone) can be inserted into chamber 172 via aperture 180.

Inflatable sac 152 is generally an inflatable balloon-type element. Inflatable sac 152 is operatively arranged between inferior component 120 and superior component 160, specifically, surface 144 and surface 166. Inflatable sac 152 comprises at least one port through which hardenable material or viscoelastic material is injected therein. The arrangement of inflatable sac 152 between inferior component 120 and superior component 160 allows prosthesis to be expanded to a customized height. For example, in the collapsed state shown in FIG. 7A, surface 166 is separated from surface 126 by height H1. In the expanded state shown in FIG. 7B, surface 166 is separated from surface 126 by height H2. Height H2 should represent the desired disc space, or the desired height of the disc that is being replaced. Inflatable sac 152, when inflated, should exhibit an elliptical or ovular or ellipsoidal cross-sectional shape. The top and bottom surfaces of inflatable sac, when inflated, are curvilinear. Specifically, inflatable sac 152 comprises a top convex surface that engages with concave surface 184 and a bottom convex surface that engages concave surface 144. The engagement of concave surfaces 144 and 184 with the convex surfaces of inflatable sac 152 allow for circumferential and translational displacement of the elements of prosthesis, thus resembling normal vertebral movement with respect to their intervertebral discs. Thus, the use of an inflatable sac operates as both an expansion mechanism (i.e., displacing superior component 160 in direction D1 with respect to inferior component 120 and thus expanding prosthesis 110 to the desired height) and a replacement intervertebral disc that allows normal vertebral movement of adjacent vertebrae (to be fused with inferior component 120 and superior component 160).

It should be appreciated that other spacing elements can be used in place of or in addition to inflatable sac 152. For example, a solid roller or spacer having convex top and bottom surfaces can be arranged between inferior component 120 and superior component 160, specifically, between surfaces 144 and 184. In such embodiments, an expansion mechanism or device can be used to displace superior component 160 with respect to inferior component 120, at which point the solid roller is arranged therebetween. Some examples of expansion mechanisms are ratcheting devices, worm drive expanders, screw and screw jack expanders, translating wedges, etc. Additionally, the size of the solid roller or spacer can be selected based on the desired disc space. Thus, solid rollers or spacers of various sizes would be available to the user at the time of insertion of prosthesis 110, and the correct size would be chosen then.

Struts 150A is operatively arranged to engage grooves 128A and 168A and strut 150B is operatively arranged to engage grooves 128B and 168B. Struts 150A and 150B are operatively arranged to be inserted into the respective grooves to prevent or limit displacement of superior component 160 relative to inferior component 120, or vice versa. Specifically, and as best shown in FIG. 7B, strut 150A is engages in grooves 128A and 168A and strut 150B is engaged in grooves 128B and 168B. As such, superior component 160 cannot be displaced in circumferential directions CD1-4 with respect to inferior component 120, and vice versa. Additionally, superior component 160 cannot be displaced in direction D2 with respect to inferior component 120 (i.e., prosthesis 110 cannot be collapsed). Struts 150A-B thus provide non-movement between vertebrae during the healing and/or fusion process.

Specifically, prosthesis 110 is inserted into a disc space between vertebrae in the collapsed state as shown in FIG. 7A. Inflatable sac 152 is then expanded to the desired height and bone material is injected into chambers 132 and 172. Struts 150A-B are then engaged in respective grooves 128A-B and 168A-B until fusion occurs between superior component 160 and its adjacent vertebra and inferior component 120 and its adjacent vertebra, at which point the healing or fusion process is complete.

In some embodiments, struts 150A-B are dissolvable or absorbable, comprising a bio tolerant material, and are absorbed after a period of time (e.g., three months). In some embodiments, the period of time is substantially equal to the time it takes for fusion or healing to occur. In some embodiments, struts 150A-B comprise polylactic acid (PLA) or polyglycolic or polyglycolide acid (PGA). It should be appreciated that the width of struts 150A-B should be substantially similar if not just less than the width of grooves 128A-B and 168A-B. The height of struts 150A-B should be that which creates the desired disc replacement height H2. Thus, the height of struts 150A-B should be roughly height H2 or slightly larger to maintain surface 166 at height H2 with respect to surface 126.

Figure 9A:
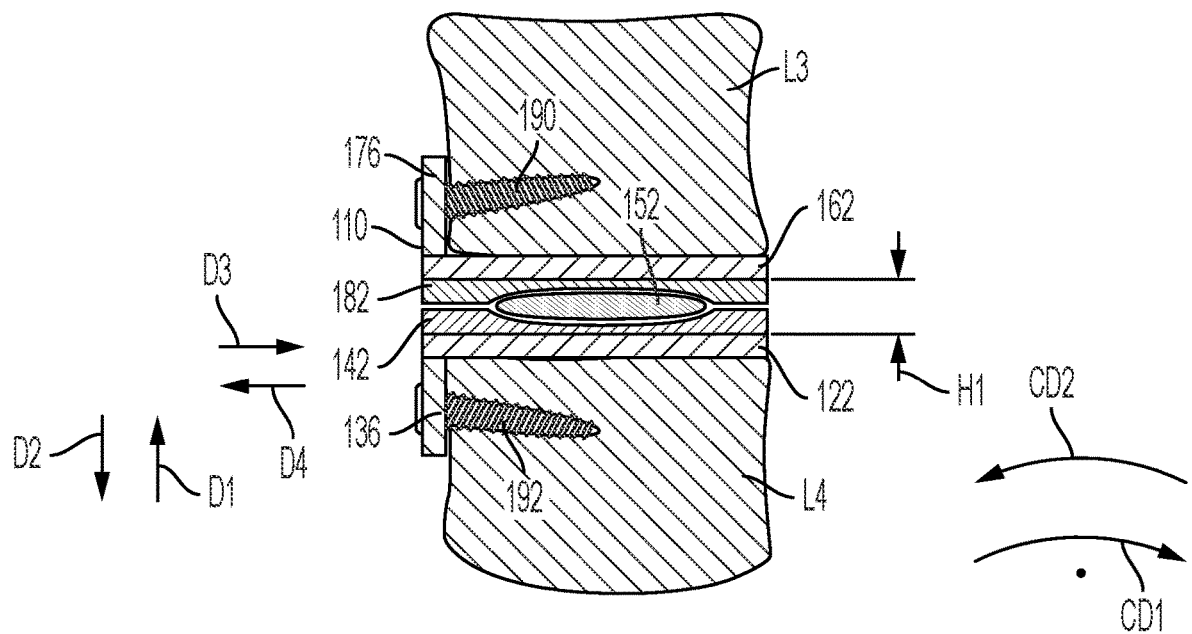
FIG. 9A is a cross-sectional view of the intervertebral disc replacement fusion prosthesis shown in FIG. 7A, engaged with vertebrae; and, FIG. 9B is a cross-sectional view of the intervertebral disc replacement fusion prosthesis shown in FIG. 7B, engaged with vertebrae.

FIG. 9A is a cross-sectional view of intervertebral disc replacement fusion prosthesis or prosthesis 110, engaged with vertebrae L3 and L4, in the collapsed state. As shown, the damaged original disc $D_{L3-4}$ is removed and prosthesis 110 is inserted between vertebrae L3 and L4. Specifically, surface 124 is engaged with vertebra L4 and surface 164 is engaged with vertebra L3. Screw 190 is fastened into vertebra L3 through hole 178 of flange 176, thus fixedly securing superior component 160 to vertebra L3. Screw 192 is fastened into vertebra L4 through hole 138 of flange 136, thus fixedly securing inferior component 120 to vertebra L4. Inflatable sac 152 is then inflated with a hardenable or viscoelastic material until the desired high of prosthesis 110 is achieved. Alternatively, or additionally, superior component 160 may be displaced in direction D1 relative to inferior component 120 via an expansion mechanism, at which point a static or solid spacer can be inserted therebetween, as previously described.

Figure 9B:
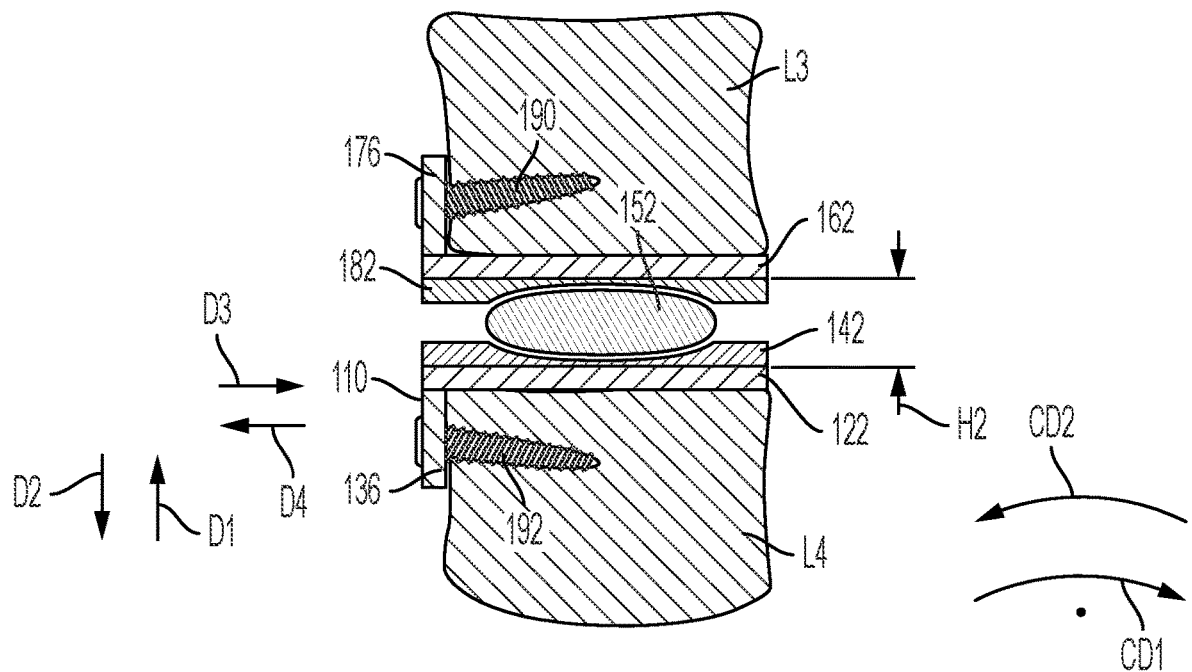

FIG. 9B is a cross-sectional view of prosthesis 110, engaged with vertebrae L3 and L4, in the expanded state. As shown, inflatable sac 152 has been filled/inflated with material such that the desired disc height is achieved. Chambers 132 and 172 are then filled with bone material via apertures 140 and 180, respectively. Then, struts 150A-B are inserted between superior component 160 and inferior component 120 as previously described, and prosthesis is left in situ. After a period of time, preferably after fusion or bone ingrowth has occurred between the injected bone material and the adjacent vertebrae and/or the hardenable martial used to inflate inflatable sac 152 has hardened and/or tissue has healed, struts 150A-B absorb or dissolve and allow for normal translational, circumferential, and compressional movement between vertebrae L3 and L4.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Spinal column
12 Ligament
C1-C7 Cervical vertebrae
T1-T12 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
SP Spinous process
TP Transverse process
IF Intervertebral foramen
NC Neural canal
A Annulus
N Nucleus
DH Disc space height
110 Intervertebral disc replacement fusion prosthesis
120 Inferior component
122 Body
124 Surface
126 Surface
128A Groove
128B Groove
130 Groove
132 Chamber
134 Apertures
136 Flange
138 Hole or holes
140 Aperture
142 Insert
144 Surface
150A Strut
150B Strut
152 Inflatable sac or sac or spacer or spacing element
160 Superior component
162 Body
164 Surface
166 Surface
168A Groove
168B Groove
170 Groove
172 Chamber
174 Apertures
176 Flange
178 Hole or holes
180 Aperture
182 Insert
184 Surface
190 Screw
192 Screw
CD1 Circumferential direction
CD2 Circumferential direction
CD3 Circumferential direction
CD4 Circumferential direction
D1 Direction
D2 Direction
D3 Direction
D4 Direction
D3 Direction
D4 Direction
H1 Height
H2 Height

What is claimed is:

1. An intervertebral disc replacement fusion prosthesis, comprising:
   an inferior component, including:
      a first top surface;
      a first bottom surface;
      a chamber arranged between the first top surface and the first bottom surface; and,
      a plurality of apertures extending from the first bottom surface to the chamber;
   a superior component, including:
      a second top surface; and,
      a second bottom surface;
   a spacing element arranged between the first top surface and the second bottom surface;
   a first insert slidingly engaged with the first top surface, the first insert including a first inner surface engaged with the spacing element; and,
   a second insert slidingly engaged with the second bottom surface, the second insert including a second inner surface engaged with the spacing element.

2. The prosthesis as recited in claim 1, wherein the spacing element comprises an inflatable sac.

3. The prosthesis as recited in claim 1, further comprising:
   at least one first groove arranged in the first top surface;
   at least one second groove arranged in the second bottom surface; and,
   a strut operatively arranged to engage the at least one first groove and the at least one second groove.

4. The prosthesis as recited in claim 3, wherein the strut prevents the superior component from displacing toward and circumferentially with respect to the inferior component.

5. The prosthesis as recited in claim 3, wherein the strut is absorbable or dissolvable.

6. The prosthesis as recited in claim 1, further comprising at least one flange extending from at least one of the inferior component and the superior component.

7. The prosthesis as recited in claim 6, wherein the at least one flange extends from the inferior component and comprises an aperture fluidly connected to the chamber.

8. The prosthesis as recited in claim 1, wherein the first inner surface and the second inner surface are concave.

9. The prosthesis as recited in claim 8, wherein the spacing element is convex in shape at its engagement with the first inner surface and the second inner surface.

10. The prosthesis as recited in claim 1, wherein the first inner surface and the second inner surface are slidingly engaged with the spacing element.

11. An intervertebral disc replacement fusion prosthesis, comprising:
    an inferior component, including:
        a first top surface;
        a first bottom surface;
        a first chamber arranged between the first top surface and the first bottom surface; and,
        a first plurality of apertures extending from the first bottom surface to the first chamber;
    a superior component, including:
        a second top surface;
        a second bottom surface;
        a second chamber arranged between the second top surface and the second bottom surface; and,
        a second plurality of apertures extending from the second bottom surface to the second chamber;
    a spacing element arranged between the first top surface and the second bottom surface; and,
    a strut engaged with the first top surface and the second bottom surface and operatively arranged to prevent the superior component from displacing toward and circumferentially with respect to the inferior component.

12. The prosthesis as recited in claim 11, wherein the spacing element comprises an inflatable sac.

13. The prosthesis as recited in claim 11, further comprising:
    at least one first groove arranged in the first top surface;
    at least one second groove arranged in the second bottom surface; and,
    the strut is operatively arranged to engage the at least one first groove and the at least one second groove.

14. The prosthesis as recited in claim 13, wherein the strut is totally absorbable or dissolvable.

15. The prosthesis as recited in claim 11, further comprising at least one flange extending from the inferior component, the at least one flange comprising an aperture fluidly connected to the first chamber.

16. The prosthesis as recited in claim 11, further comprising:
    a first insert slidingly engaged with the first top surface, the first insert including a first concave inner surface engaged with the spacing element; and,
    a second insert slidingly engaged with the second bottom surface, the second insert including a second concave inner surface engaged with the spacing element.

17. The prosthesis as recited in claim 16, wherein:
    the spacing element is convex in shape at its engagement with the first inner surface and the second inner surface; and,
    the first inner surface and the second inner surface are slidingly engaged with the spacing element.

18. An intervertebral disc replacement fusion prosthesis, comprising:
    an inferior component, including:
        a first top surface;
        a first bottom surface;
        a first chamber arranged between the first top surface and the first bottom surface; and,
        a first plurality of apertures extending from the first bottom surface to the first chamber;
    a superior component, including:
        a second top surface;
        a second bottom surface;
        a second chamber arranged between the second top surface and the second bottom surface; and,
        a second plurality of apertures extending from the second bottom surface to the second chamber;
    a first insert slidingly engaged with the first top surface;
    a second insert slidingly engaged with the second bottom surface; and,
    an inflatable sac arranged between the first insert and the second insert;
    wherein:
        in an unlocked state, the superior component is translationally and circumferentially displaceable relative to the inferior component; and,
        in a locked state, at least one strut is engaged with the first top surface and the second bottom surface to prevent the superior component from displacing toward and circumferentially with respect to the inferior component.

* * * * *